(12) United States Patent
Jungheim et al.

(10) Patent No.: US 8,372,359 B2
(45) Date of Patent: Feb. 12, 2013

(54) SAMPLE VIAL RETAINER

(75) Inventors: Bert Jungheim, Boyds, MD (US); Andrew Leonard, Sykesville, MD (US)

(73) Assignees: Qiagen Gaithersburg, Inc., Gaithersburg, MD (US); Bert Jungheim, Boyds, MD (US)

( * ) Notice: Subject to any disclaimer, the term of this patent is extended or adjusted under 35 U.S.C. 154(b) by 602 days.

(21) Appl. No.: 12/622,140

(22) Filed: Nov. 19, 2009

(65) Prior Publication Data

US 2011/0116994 A1   May 19, 2011

(51) Int. Cl.
*B01L 9/06* (2006.01)
(52) U.S. Cl. .................... 422/562; 422/300; 435/809
(58) Field of Classification Search .............. 422/300, 422/560–562; 435/809
See application file for complete search history.

(56) References Cited

U.S. PATENT DOCUMENTS

| | | | |
|---|---|---|---|
| 3,350,946 A | 11/1967 | Isreeli | |
| 3,724,638 A | 4/1973 | Peters et al. | |
| 4,155,711 A | 5/1979 | Zelagin et al. | |
| 4,453,639 A * | 6/1984 | Sharma | 211/74 |
| 5,008,082 A | 4/1991 | Shaw | |
| 6,086,827 A | 7/2000 | Horner et al. | |
| 2008/0075634 A1* | 3/2008 | Herchenbach et al. | 422/104 |

OTHER PUBLICATIONS

International Search Report from PCT/US10/57469 mailed Jan. 24, 2011.

* cited by examiner

*Primary Examiner* — In Suk Bullock
*Assistant Examiner* — Paul Hyun
(74) *Attorney, Agent, or Firm* — RatnerPrestia

(57) ABSTRACT

A vial retainer system for an automated processing apparatus. The vial retainer system includes a track mounted to the processing apparatus, a rack adapted to slide in a longitudinal direction on the track, and a vial retainer positioned over the rack. The rack is movable in a distal direction to install the rack on the processing apparatus, and in a proximal direction, opposite the distal direction, to remove the rack from the processing apparatus. The rack is adapted to hold one or more vials in an upright orientation. The vial retainer has one or more a sloped surfaces inclined such that a distal end of each sloped surface is closer to the track than a proximal end of each sloped surface.

28 Claims, 2 Drawing Sheets

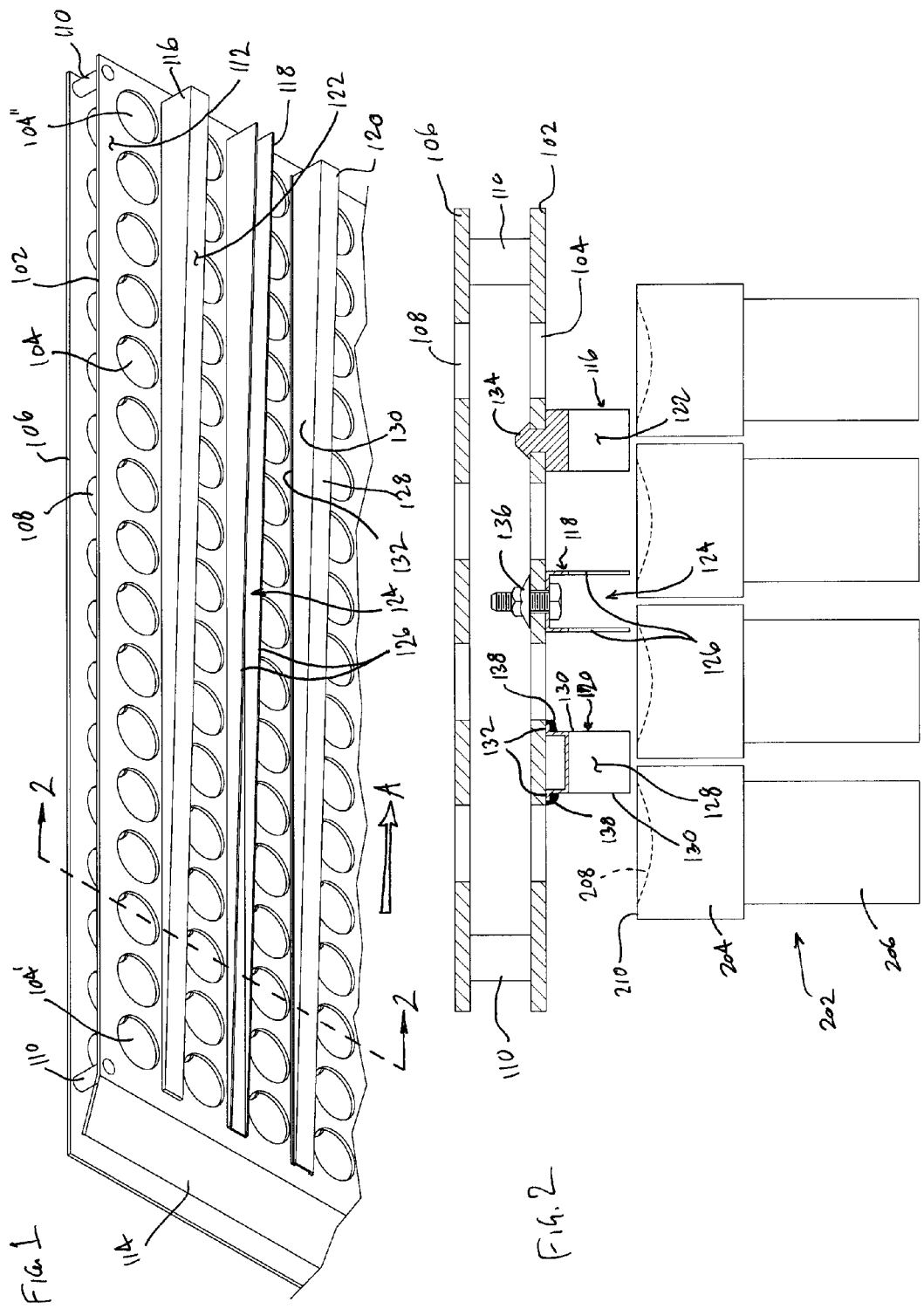

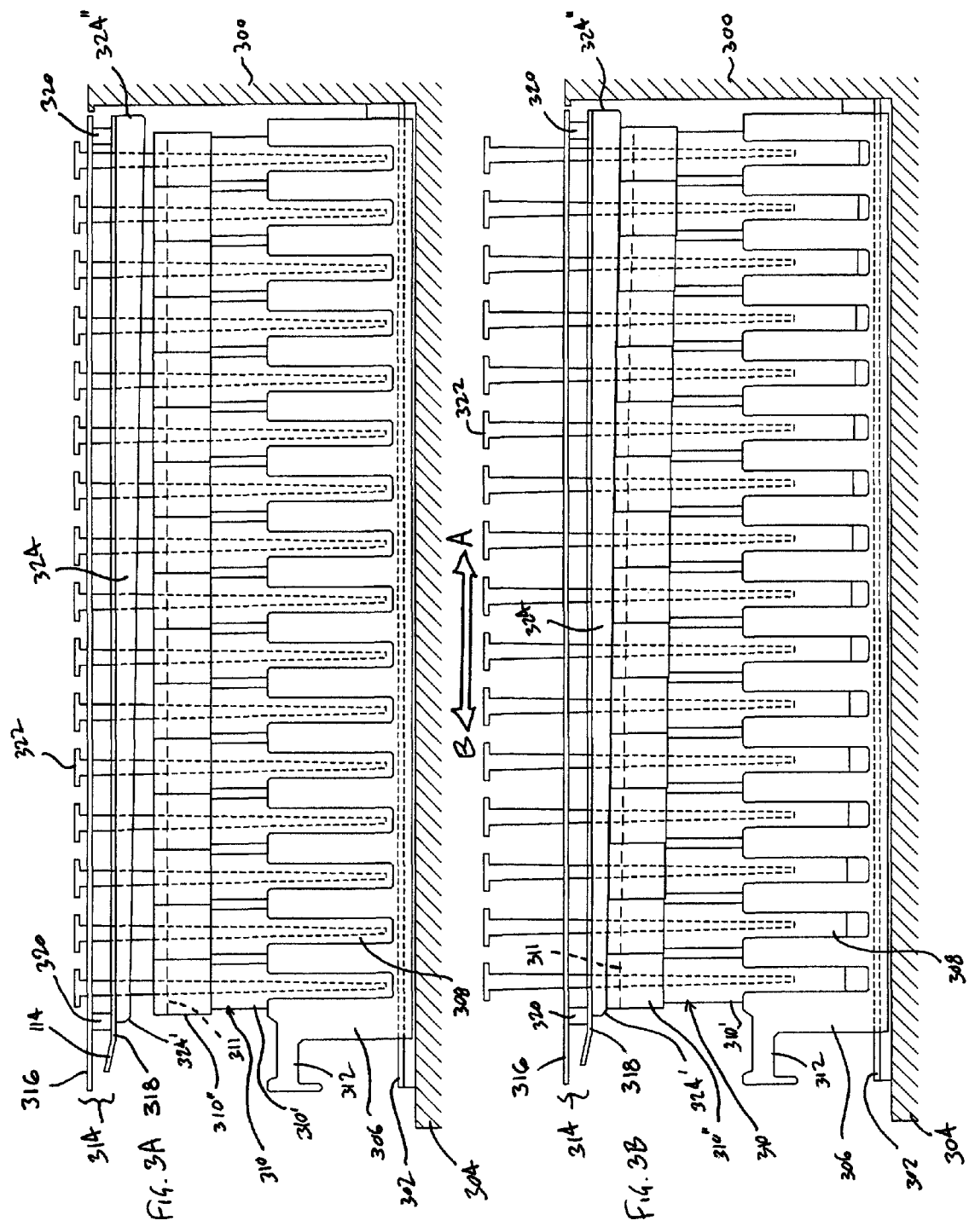

SAMPLE VIAL RETAINER

BACKGROUND

1. Field of the Art

The present application relates to clinical testing systems, and in particular to test systems in which sample containers are processed using pipettors or other devices that may tend to lift the sample containers. Other uses will, however, be readily apparent from the present disclosure.

2. Description of Related Art

Medical sample processing equipment often includes pipettors, aspirators, and other devices to remove substances from and add substances to containers. For example, it is known to aliquot specimens from biological sample containers using a pipette, and to aspirate wash buffers or other fluids from containers during processing. it is also known to add fluid to containers using pipettes, nozzles, and the like. Typical containers vary in size and shape. Typical containers can hold blood, urine, liquid-based cytology (LBC) samples containing tissue or other matter, reagents, buffers, control samples, calibration samples, and so on.

In many instances pipetting, aspirating and other fluid withdrawal processes are simple and straightforward operations with little complication. This is particularly true where the container is firmly held during the process, and there is little likelihood that the pipettor or aspirator will contact or move the container. However, where large numbers of containers are being processed, it may be cumbersome to affix each container to a rack or other surface or structure (using threads or cam-locks, for example) to hold them down during processing. Thus, it is often preferred to hold containers by slipping them with little friction into form-fitting wells.

Some containers, however, may not be held firmly during a pipetting or aspirating process, making them more susceptible to movement due to contact by the fluid removal device. Such contact may lead to spills or unwanted movement. In addition, some containers may include a foam, foil and/or elastic cover through which the pipettor or aspirator passes to access the container's contents. Examples of such containers are found in U.S. Pat. Nos. 6,752,965; 6,030,582; 5,514,339; 5,370,252; 5,297,599; 4,243,150 and 3,088,615, which are incorporated herein by reference. Still other containers are shown and described in European Patent Nos. 0 115 480 and 0 081 976; and International Application No. WO 00/69389. Some of these seals are intended to re-close, at least to some degree, after the pipette or aspirator are removed from the container to help prevent evaporation, cross-contamination, or inadvertent loss of the contents. As such, the cover may exert a restoring force against the pipettor or aspirator, creating friction between the two during insertion or removal. Even foil seals, which tend to deform plastically without generating a significant restoring force, can still catch on or grip a pipette or aspirator as it is removed.

Contact between a cover and a pipette or aspirator can generate a significant force that can move the container. For example, contact between a cover and a pipette may lift a container partly or entirely out of a container rack or tray holding the container. In view of this, some form of retainer may be used to hold the container down as the pipette or aspirator is being removed. In manual processes, the retainer typically is a person's hand. In automated processes, a typical retainer may be a flat panel located over a rack of containers. The panel may have notches or holes through which the pipettes or aspirators access the containers, but these holes or notches are small enough or shaped to prevent the container from rising above a predetermined height as the pipette or aspirator is removed.

Although prior retainers may be effective in some circumstances, it has been determined that there is a need for alternative retaining systems to hold sample containers as devices such as pipettes, aspirators, and the like are being withdrawn form the container. The following description provides exemplary embodiments of alternative retaining systems.

SUMMARY

The present disclosure provides a number of inventions that may be used collectively, in various combinations, or alone. The following summary provided examples of such inventions, and does not limit the invention as claimed in any way.

In one exemplary aspect, there is provided a vial retainer system for an automated processing apparatus. The vial retainer system includes a track mounted to the processing apparatus, a rack adapted to slide in a longitudinal direction on the track, and a vial retainer positioned over the rack. The rack is movable in a distal direction to install the rack on the processing apparatus, and in a proximal direction, opposite the distal direction, to remove the rack from the processing apparatus. The rack is adapted to hold one or more vials in an upright orientation. The vial retainer has one or more a sloped surfaces inclined such that a distal end of each sloped surface is closer to the track than a proximal end of each sloped surface.

BRIEF DESCRIPTION OF THE DRAWINGS

FIG. 1 is a fragmented isometric view of a panel having several embodiments of vial retainers attached thereto.

FIG. 2 is a front elevation view of a panel having several embodiments of vial retainers attached thereto.

FIGS. 3A and 3B are side elevation views of a panel having an embodiment of a vial retainer attached thereto, and a sample rack having a number of vials shown in a lowered position (FIG. 3A) and an elevated position (FIG. 3B).

DETAILED DESCRIPTION OF EXEMPLARY EMBODIMENTS

The embodiments described below generally provide a vial retainer adapted to hold sample vials against excessive movement, and at the same time provide at least some degree of contamination prevention. Typical medical sample processing systems handle a large number of sample vials at the same time. Such vials may be installed in a processing system on racks holding a number of individual sample vials. A typical initial or early step in many sample processing systems is to aliquot a specimen from each sample vial. The specimen is then processed, and the sample vial can be removed and archived. If additional testing or retesting is needed for a sample, the sample vial can be recovered from the archive and re-processed.

As noted above, in some instances a pipette used to aliquot a specimen from a sample vial may interact with the vial's lid, and may pull the vial out of a rack holding the vial in place. To prevent vials from being completely removed, which could cause spills or other problems, a typical sample processing system may place a panel over the vials to hold the vials down as the pipette is removed. A typical panel comprises a flat sheet of metal or plastic having a number of holes through which the pipette can access each vial.

It has been found that such panels can create problems when used in automated processing systems. In particular, vial retainer panels typically have a flat lower surface that the vials contact if they are lifted by a pipettor or other device. As the vials contact the surface, fluids that may be present on the tops of the sample vials may contact and adhere to the surface. When the vials are removed from below the panel, which may be done by sliding them on a rack that moves perpendicular to the panel, they can contact fluid from other vials, potentially causing cross-contamination of the samples contained in the vials. If a sample is contaminated in this manner, the reliability of any later test performed on that sample is suspect, and may be invalid. Furthermore, the contamination may go undetected.

In addition to potentially causing cross-contamination, fluid adhering to the retainer panel can create a messy and, ultimately, unclean environment in a test apparatus. Such fluid can make surfaces slippery, attract dust, foster mildew or mold growth, contaminate other parts the equipment, increase risk of exposing human operators to potentially hazardous materials, and cause other problems. Thus, even if the vials contain substances for which cross-contamination is not a concern (e.g., they all contain the same reagent or buffer), fluid adhering to the panel still is a problem. Of course, this problem also exists in systems in which the samples are discarded after testing, and not used for retesting in any event.

Referring now to FIGS. 1 and 2, it has been found that the problem of fluids and other substances adhering to a vial retainer panel can be alleviated, at least to some degree, by providing one or more ramped vial retainers on the bottom of the retainer panel. As shown in FIG. 1, a typical retainer panel 102 comprises a flat panel having a number of holes 104 through which pipettes, aspirators, nozzles or other devices (not shown) can access sample vials. The view in FIG. 1 shows the bottom surface 112 of the retainer panel 102.

The retainer panel 102 in this exemplary embodiment is suspended beneath a cover panel 106 having holes 108 corresponding to the holes 104 on the retainer panel 102. The two panels 102, 106 are connected by a number of pins 110, posts, screws, bolts or other fasteners, which provides stiffness to the assembled panel structure, and may be helpful to establish a vertical offset between the two panels. If desired, the spacing between the two panels 102, 106 may be adjustable, which may be accomplished by connecting them with threaded rods or replaceable spacers. In other embodiments, the retainer panel 102 may be a standalone panel, or attached to another panel or other structural support in other ways. Similarly, the illustrated holes 104, 108 are exemplary, and other shapes, sizes and patterns of holes may be used. For example, groups of holes may be replaced by slots.

If desired, the retainer panel 102 may include an elevated lip 114 to help guide samples beneath it. The lip 114 is positioned below the cover panel 106, which remains flat over the lip 114 to provide a flat area above the panels. Having a flat area over the panels typically may be desirable to permit objects to rest on the panel without rolling or tipping, or to keep the area free of obstructions that may interfere with automated equipment such as pipettors.

FIG. 1 illustrates three embodiments of vial retainers 116, 118, 120 that may be attached to or formed on the bottom of the retainer panel 102 to help alleviate the problem of adhering fluid causing cross-contamination or generally being distributed by incoming and outgoing sample vials. Each exemplary vial retainer 116, 118, 120 comprises a structure positioned between adjacent rows of holes 104. The vial retainers 116, 118, 120 extend parallel to the direction in which vials are moved to position the vials below the retainer panel 102. This direction is shown by arrow A. Each vial retainer 116, 118, 120 may extend substantially the full distance from the first hole 104' to the last hole 104" in each row, although it may not be necessary for the retainers to extend to the first hole 104'. While the vial retainers 116, 118, 120 may be interrupted along their length, it is more preferred for them to be substantially continuous along their entire length.

Referring now to FIG. 2, exemplary constructions for the vial retainers 116, 118, 120 are described in detail. FIG. 2 illustrates the embodiment of FIG. 1, shown along line 2-2 in FIG. 1.

The first exemplary vial retainer 116 may comprise a simple solid block of material that is machined, molded or otherwise formed to have a smooth ramp 122 along its bottom surface. The ramp 122 may be flat, curved, or formed of a series of angled or flat steps. If the ramp 122 has angled or flat steps, it is preferred for the transition between adjacent steps to have a slope or bevel to help prevent vials from striking and stopping at these transitions during installation. Preferably, the ramp 122 is a simple planar structure.

As shown in FIG. 2, the ramp 122 is wide enough to contact at least one vial 202 as the vial is raised by a pipettor (not shown) or other device. Where a lid 204 is provided on the vial, the ramp 122 may contact the lid 204. In some cases, the vial 202 may not have a lid when it is installed, or the lid may comprise a simple foil covering, in such cases the ramp 122 may contact the tube 206 portion of the vial 202. In many instances in which a vial lid 204 is intended to be pierced by a pipette tip, the lid 204 has a depressed portion 208 surrounded by a raised rim 210. In such embodiments, the ramp 122 will contact only the raised rim 210—preferably generally only along an outer edge thereof. In these embodiments, any escaped fluid that may end up on the lid 204 is likely to settle in the depressed portion 208, and remain out of contact with the ramp 122. This may be the case even if there is enough escaped fluid to fill the depressed portion 208, or form a meniscus that reaches all the way up the depressed portion 208. To further enhance the operation of the ramp 122, the lid 204 may be modified by including one or more raised structures or crenellations that contact the ramp 122, but permit fluid to flow off the lid without contacting the ramp 122.

The second vial retainer 118 is similar to the first vial retainer 116, but instead of being a solid block of material it has a downward-facing channel 124 having one relatively narrow ramp 126 on one lateral side, and another relatively narrow ramp 126 on the other lateral side. The ramps 126 may have the same ramp profile, or different profiles, and may have any suitable shape as described previously herein. Care may be used to ensure that the ramps 126 are not so narrow or sharp that they damage or catch on the vials 202, or that they are too easily bent. As steel channel having a wall thickness of about 0.30 inches and squared edges is believed to be suitable for use with nylon or other plastic vials. Additionally, sides of lateral sides 126 may be bent inward or outward to form landings (not shown) that may facilitate contact with vials, help provide structural reinforcement, or help decrease the likelihood that they damage or catch on the vials 202.

The third vial retainer 120 is similar to the second vial retainer 118 in that it is formed from a channel, but in this case the channel opens upward so that the flat face of the channel forms a ramp 128. The sides 130 of the channel extend upwards and are connected to the retainer panel 102. To facilitate this connection, the channel sides 130 may be bent inward or outward to form landings 132 that rest against the retainer panel 102.

The vial retainers 116, 118, 120 may be made of any suitable material, such as metal (e.g., aluminum, steel, brass, etc.), plastic (vinyl, nylon, acetal homopolymer (i.e., Delrin™), teflon-impregnated plastic, PTFE, etc.), wood, ceramic, composite materials, or other suitable materials. If desired, the vial retainers 116, 118, 120 may be treated to reduce friction, and may be treated to have hydrophobic properties to help prevent fluid from adhering to it. Certain embodiments of the vial retainers 116, 118, 120 may lend themselves to particular materials or construction techniques. For example, the first vial retainer 116 may be easily molded or machined from a soft material such as Delrin™ or vinyl, whereas the second and third vial retainers may be easily machined from aluminum extrusions or formed from pre-existing steel or aluminum channel stock. The selection of construction methods, materials, and the like will be understood by persons of ordinary skill in the art in view of this disclosure, and need not be described in detail here.

The vial retainers 116, 118, 120 may be secured to the retainer panel 102 in any suitable way. For example, the first vial retainer 116 may be formed of a plastic material and have deformable snap pins 134 integrated into its upper face to engage corresponding holes through the retainer panel 102. As another example, the second vial retainer 118 may be secured to the retainer panel 102 by one or more threaded fasteners 136 (e.g., screws or bolts secured into threads formed in the parts or by nuts or locknuts), rivets or other conventional fastening devices. As still another example, the third vial retainer 120 may be secured to the retainer panel 102 by welds 138. Still other variations are possible. For example, the sides 130 of the third vial retainer 120 may have protrusions that snap into slots in the retainer panel 102, or the vial retainers 116, 118, 120 may be secured to the retainer panel 102 using adhesives or a combination of connection techniques. Under readily appreciated suitable circumstances, virtually any combination of attachment techniques may be used to hold any of the vial retainers 116, 118, 120 to the retainer plate.

Vial retainers 116, 118, 120 may be provided between each adjacent row of holes 104 so that each retainer contacts vials 202 in each row, as shown in FIG. 2. Alternatively, vial retainers 116, 118, 120 may be placed only between every other adjacent pair of rows, so that each vial 202 is retained by a single retainer. Vials on the end rows may only be contacted by a single retainer, as shown, or another retainer may be added outside each end row. In other embodiments, the vial retainers 116, 118, 120 may extend directly across a row of holes 104, in which case the vial retainers 116, 118, 120 should have an opening at each hole location to permit the necessary equipment to pass through to the vials 202. The second vial retainer 118 may be particularly suited to such a modification, but other vial retainer constructions may be used.

Other shapes, constructions and attachments for other embodiments of vial retainers will be readily apparent in view of the present disclosure. For example, a vial retainer may be formed using an right-angle shape, as opposed to a channel, having one surface attached to the retainer plate 102, and the other surface extending towards the vials 202. As another example, a vial retainer may be formed from one or more metal wires or straps extending along, but at an angle to, the bottom of the retainer plate 102. A vial retainer formed from a wire or strap may be shaped, something like a ski, with an upturned end. In addition, a vial retainer may be attached to something other than the retainer panel, and the retainer panel and/or cover panel may be omitted entirely.

FIGS. 3A and 3B illustrate aspects of the operation of an exemplary embodiment of a vial retainer used in an exemplary sample processing apparatus 300. The sample processing apparatus 300 may comprise any equipment used to process multiple samples mounted on a rack that holds one or more sample vials in a linear or two-dimensional array. Examples of processing equipment and racks with which embodiments may be used are shown, for example, in U.S. application Ser. No. 12/588,304, filed Oct. 9, 2009; U.S. application Ser. No. 12/622,131 entitled "Multiple-Input Analytical System" filed on Nov. 19, 2009; U.S. application Ser. No. 12/622,150 entitled "Sampling Devices and Methods" filed on Nov. 19, 2009; and U.S. application Ser. No. 12/617,485 entitled "Sample Rack System" filed on Nov. 12, 2009. The foregoing applications are incorporated herein by reference in their entireties.

The processing apparatus 300 includes one or more sample tracks 302 mounted on a platform 304. The platform 304 and tracks 302 preferably are located such that they can be accessed from one side of the apparatus 300, and may be covered by a removable panel or door (not shown). Racks 306 are provided to move along the tracks 302. Each rack moves in a generally linear direction during installation and removal. Arrow head "A" shows the installation direction, and arrow head "B" shows the removal direction. The tracks 302 and racks 306 may have any suitable devices or combinations of devices to cause the racks 306 to slide along the tracks 302 in a controlled manner. For example, the track 302 may comprise a "T"-shaped protrusion, and the rack 306 may have a corresponding "T"-shaped groove along its bottom surface that envelopes the "T"-shaped track 302 and limits or prevents unwanted lateral and vertical movement. Each rack 306 has multiple sample wells 308 adapted to receive respective vials 310 and hold the vials 310 upright. The wells 308 may be arranged in one or more rows that extend generally along the length of the rack 306 and along the installation direction (arrow A-B). Each rack 306 also may have a handle 312 to manipulate the rack 306. Sample vial racks 306 and corresponding tracks 302 as described above are known in the art, and any variation of the illustrated embodiment may be used.

The vials 310 may comprise any known or later-developed vial or vial system. For example, the vials 310 may include a container body 310' having a removable lid 310". The lid 310" optionally may be removed before processing. The lid 310" or top of the container body 310' may have a pre-pierced or pierceable membrane, paper or foil seal, foam layer, or other cover 311 through which a pipette tip 322 or other device must pass to access the contents of the vial 310. Friction or other contact between the cover 311 and the pipette tip 322 or other device may lift the vial 310 as the pipette tip 322 or other device is removed in the upward direction. The vial 310 may contain any substance, such as a patient sample or other test sample, a control or calibrator, a reagent or buffer, and so on.

A panel assembly 314 is mounted above the platform 304 to form an enclosed or partially-enclosed sample bay. The panel assembly 314 may comprise an upper panel 316 and a lower panel 318 suspended below the upper panel 316 by one or more posts 320. The gap between the upper and lower panels 316, 318 may be adjustable, if desired. Each panel 316, 318 includes one or more holes, slots, cutouts or the like (see, e.g., FIG. 1) that permit pipettes, aspirators, nozzles, or other devices, to extend down into the vials 310. In the shown embodiment, multiple pipette tips 322 are simultaneously lowered into each vial 310 to access multiple specimens, but a single pipette tip 322 or other numbers of tips may be used in other embodiments.

A vial retainer 324 is mounted to the bottom of the lower panel 318. The vial retainer 324 has a ramped shape that gradually descends along the installation direction (arrow A) such that its leading edge 324' is higher than its trailing edge

324". The vial retainer 324 may have any suitable ramp shape, size, construction and mounting arrangement. The reader is referred to the various examples of vial retainer constructions that are described elsewhere herein as exemplary embodiments for the vial retainer 324.

FIG. 3A illustrates the rack 306 and vials 310 as they may appear when they are initially installed in the processing apparatus 300. As shown, each vial 301 may be seated at the bottom of each well 308, although some lifting may be present as a result of moving the rack and vials or not fully seating the vials 310 in the first place, or due to preceding processes such as mixing. In use, pipette tips 322 or other devices are lowered into the vials 310, such as shown in FIG. 3A. As the pipette tips 322 or other devices are removed, they tend to lift the vials 310. As shown in FIG. 3B, the vials 310 eventually contact the vial retainer 324, which stops their upward movement. Due to the ramp-like shape, each vial 310 is stopped at a slightly different level, with the more distal vials 310 (i.e., those furthest along the installation direction shown by arrow A) being stopped at the lowest elevation, and each consecutive proximal vial 310 being stopped at a slightly higher elevation. Once the pipette tips 322 are removed, the force lifting the vials 310 may terminate, and the vials 310 may fall partly or entirely back into the wells 308. However, where the wells 308 and vials 310 have a relatively tight fitment tolerance, the vials 310 may remain elevated at the level of the vial retainer 324 even after the pipette tips 322 are removed. It will be appreciated that FIG. 3B is exemplary, and some or even all of the vials 310 may not rise at all as the pipette tips 322 are removed, or they may not rise all the way to the vial retainer 324 before falling back into their respective wells 308.

After processing is complete, each rack 306 is removed from the processing apparatus 300 by sliding it backwards along the tracks 302. The racks 306 move in a proximal removal direction (arrow B) that is generally linear and opposite the distal installation direction (arrow A). As the rack 306 is removed, any vials 310 that are still contacting the vial retainer 324 will quickly separate from the vial retainer 324, due to the vial retainer height increasing relative to the vial heights as the rack 306 moves proximally off of the platform 304. Preferably, each vial 310 breaks contact with the vial retainer 324 before contacting any portions of the vial retainer 324 against which the more proximal other vials 310 were in contact. Thus, if liquids or other substances escape from a vial and adhere to the vial retainer 324, the more distal vials 310 are less likely to contact the substance as they will pass below it as the rack 306 is removed. This decreases the possibility that escaped liquids or other substances will contact and possibly contaminate other vials 310, and also reduces the likelihood that substances will be smeared along the bottom of the vial retainer 324.

Placing the vial retainer 324 to the sides of the tube centerlines, as shown in FIG. 2 for example, may have the added benefit that escaped fluid that does adhere to the vial retainer 324 may only contact the outer perimeter of another vial, instead of contacting the center of the lid as might happen with a conventional retainer panel. Fluid at the edges of the lid (e.g., on a raised rim 210) is less likely to enter the vial and contaminate the contents.

The slope of the vial retainer 324 may be selected according to any suitable criteria. For example, where a vial retainer 324 is retrofitted to an existing panel assembly 314, the slope may be limited by the space available between the lower panel 318 and the tops of the vials 310. Other variables that may be considered when selecting a slope are the viscosity, surface tension, and other physical properties of a fluid in the vials 310, as a well as the typical escaped fluid volume. For example, where the fluid tends to escape in quantities that form relatively large drops on the bottom of the vial retainer 324, a larger slope may be desirable to prevent distal vials from contacting such relatively large drops. However, if the fluid properties make it likely that gravity will pull fluid drops down the slope of the vial retainer 324, as smaller slope may be desirable to prevent such movement or flat or nearly flat spots may be provided along the slope at which such movement will stop. Other design variables will be apparent to persons of ordinary skill in the art in view of the present disclosure. In one exemplary embodiment, in which sixteen vials 306 have a diameter of about 0.75 inches and are closely spaced along a rack 306, the vial retainer 324 may have a total height (i.e., distance from the lowest portion of the slope to the lower surface of the lower panel 318) of about 0.315 inches and a slope angle of about 0.45 degrees to about 2.0 degrees. Of course, other slopes are possible in other embodiments.

In some embodiments, drip points may be provided along the bottom of the vial retainer 324 to create locations where fluid accumulates to drip off the vial retainer 324. A drip point may be formed, for example, by forming a notch in the ramp surface to create a local low point where fluid will naturally accumulate. Such a drip point may be treated to have surface characteristics, such as hydrophobicity, to help initiating dripping. In other embodiments, the drop point may have a hydrophilic characteristic so that fluid tends to accumulate due to the shape of the drip point, but also tends to remain in contact with the surface.

As shown in FIGS. 3A-3B, the rack 304 may slide on a track 306. In other embodiments, the rack may be mounted to the processing apparatus by means other than a track. For example, the rack may be slid into place on a smooth platform, and locked in place with one or more fasteners or retainer. In another exemplary embodiment, the track may comprise open channels into which racks can be lowered vertically before lowering the panel assembly into place. The racks may then be removed by sliding them out from under the panel assembly, without having to remove the panel assembly. As another example, the rack or racks may move laterally, rotate, or have any other combination of movements as they are loaded onto the platform. For example, the rack may comprise a semi-circular shape (as viewed from above) that moves on a similarly curved track during loading. In addition, while the shown vial retainers are illustrated spanning multiple vials, it will be appreciated that they span or act on only a single vial. For example, the rack may be moved perpendicular to the direction shown in FIGS. 3A and 3B (i.e., into or out of the page), and the vial retainers may be turned perpendicular to their shown direction and each act on only one vial with respect to the direction of movement (the retainers may act on two side-by-side vials, however). In another embodiment, the panel assembly may be omitted, and the vial retainers may be mounted to a frame or other structure to hold them in place. Other embodiments will be apparent to persons of ordinary skill in the art in view of the present disclosure.

In the shown embodiments, each vial 310 is held in its own respective well 308, but this is not required in all embodiments. for example, a single elongated well may be provided with protrusions or other shapes that hold each vial 310 in a particular location. Alternatively, the wells 308 may be replaced by clips or other fasteners that hold the vials. The wells 308 also may include springs that elevate and possibly center each vial 310. In such an embodiment, the vials 310 may be spring-loaded in a raised position, and pushed downward by contact with the vial retainer 324 as the rack 306 is moved distally onto the platform 304. Other variations will be apparent to persons of ordinary skill in the art in view of the present disclosure.

It will be understood that the foregoing embodiments are exemplary only, and other embodiments will be apparent to those of ordinary skill in the art in light of the teachings provided herein. For example, while the foregoing embodiments describe systems and methods for use in medical sampling procedures, it will be readily apparent that these may be modified for use in other processes. Other variations will be apparent to those of ordinary skill in the art in view of the present disclosure and with practice of the invention.

The invention claimed is:

1. A vial retainer system for an automated processing apparatus, the vial retainer system comprising:
 a sample rack platform;
 a panel located over the sample rack platform;
 a vial retainer mounted on a lower surface of the panel and positioned over and spaced from the sample rack platform, the vial retainer having a proximal end and a distal end, the distal end being spaced in an axial direction from the proximal end;
 a sample container rack configured to hold one or more sample vials in an upright orientation extending from the sample rack platform towards the vial retainer, the sample container rack further being configured to slide between the sample rack platform and the vial retainer in a first direction along the axial direction from the proximal end of the vial retainer to the distal end of the vial retainer to install the sample container rack, and in a second direction, opposite the first direction, to remove the sample container rack;
 wherein the vial retainer comprises one or more sloped lower surfaces that are inclined such that a distal end of each sloped surface is closer to the sample rack platform than a proximal end of each sloped surface.

2. The vial retainer system of claim 1, wherein the sample rack platform comprises a track, and the sample container rack is adapted to slide on the track.

3. The vial retainer system of claim 2, wherein the track comprises one or more t-shaped members and the sample container rack comprises a slot adapted to envelop the one or more t-shaped members.

4. The vial retainer system of claim 1, wherein the sample container rack comprises one or more wells configured to hold the one or more sample vials.

5. The vial retainer system of claim 1, wherein the panel comprises a panel assembly having an upper panel and a lower panel.

6. The vial retainer system of claim 1, wherein the panel comprises one or more holes located above the sample container rack when the sample container rack is installed.

7. A vial retainer system for an automated processing apparatus, the vial retainer system comprising:
 a sample rack platform;
 a panel located over the sample rack platform;
 a vial retainer mounted on a lower surface of the panel and positioned over and spaced from the sample rack platform, the vial retainer having a proximal end and a distal end;
 a sample container rack configured to hold a plurality of sample vials in an upright orientation extending from the sample rack platform towards the vial retainer, the sample container rack further being configured to slide between the sample rack platform and the vial retainer in an installation direction from the proximal end of the vial retainer to the distal end of the vial retainer, and in a removal direction opposite the installation direction;
 wherein the vial retainer comprises one or more lower surfaces that slope downwardly in the installation direction.

8. The vial retainer system of claim 7, wherein the vial retainer extends linearly from the proximal end to the distal end.

9. The vial retainer system of claim 7, wherein the sample container rack comprises one or more wells configured to hold the one or more sample vials.

10. The vial retainer system of claim 7, wherein the panel comprises one or more holes located above the sample container rack when the sample container rack is installed to provide access in a vertical direction to the plurality of sample vials.

11. The vial retainer system of claim 7, wherein a plurality of sample vials are provided in the sample container rack and the one or more lower surfaces are offset from a centerline of each of the plurality of sample vials.

12. The vial retainer system of claim 7, wherein the vial retainer system comprises a plurality of vial retainers and a plurality of sample container racks.

13. The vial retainer system of claim 7, wherein the one or more lower surfaces comprise at least one planar ramp extending continuously from the proximal end of the vial retainer to the distal end of the vial retainer.

14. The vial retainer system of claim 7, wherein the vial retainer comprises a downwardly-facing channel having first and second downwardly-extending portions forming a first lower surface and a second lower surface.

15. The vial retainer system of claim 7, wherein the vial retainer comprises hydrophobic properties or hydrophilic properties.

16. The vial retainer system of claim 7, wherein the one or more lower surfaces have a slope of about 0.45 degrees to about 2.0 degrees.

17. A vial retainer system for an automated processing apparatus, the vial retainer system comprising:
 a sample rack platform;
 a panel located over the sample rack platform;
 a plurality of vial retainers mounted to a lower surface of the panel and spaced from the sample rack platform, each vial retainer having a proximal end and a distal end;
 a plurality of sample container racks each configured to hold a plurality of sample vials in an upright orientation extending from the sample rack platform towards the panel, each sample container rack further being configured to slide between the sample rack platform and at least one vial retainer in an installation direction from the proximal end of the vial retainer to the distal end of the vial retainer, and in a removal direction opposite the installation direction;
 wherein each vial retainer comprises one or more lower surfaces that slope downwardly in the installation direction.

18. The vial retainer system of claim 17, wherein the plurality of vial retainers extend linearly from its respective proximal end to its respective distal end, and the plurality of sample container racks are configured to slide in a straight line in the installation direction.

19. The vial retainer system of claim 17, wherein the panel comprises a row of holes located above each sample container rack when the sample container rack is installed to provide access in a vertical direction to the plurality of sample vials.

20. The vial retainer system of claim 17, wherein the one or more lower surfaces of at least one of the vial retainers are positioned above the plurality of sample vials contained in two adjacent sample container racks.

21. A vial retainer system for an automated processing apparatus, the vial retainer system comprising:
   a sample rack platform;
   a vial retainer positioned over and spaced from the sample rack platform, the vial retainer having a proximal end and a distal end;
   a sample container rack configured to hold a plurality of sample vials in an upright orientation extending from the sample rack platform towards the vial retainer, the sample container rack further being configured to slide between the sample rack platform and the vial retainer in an installation direction from the proximal end of the vial retainer to the distal end of the vial retainer, and in a removal direction opposite the installation direction;
   wherein the vial retainer comprises one or more lower surfaces that slope downwardly in the installation direction at a slope of about 0.45 degrees to about 2.0 degrees.

22. The vial retainer system of claim 21, wherein the vial retainer extends linearly from the proximal end to the distal end.

23. The vial retainer system of claim 21, wherein the sample container rack comprises one or more wells configured to hold the one or more sample vials.

24. The vial retainer system of claim 21, wherein the vial retainer is mounted on a lower surface of a panel located over the sample rack platform.

25. The vial retainer system of claim 24, wherein the panel comprises one or more holes located above the sample container rack when the sample container rack is installed to provide access in a vertical direction to the plurality of sample vials.

26. The vial retainer system of claim 21, wherein a plurality of sample vials are provided in the sample container rack and the one or more lower surfaces are offset from a centerline of each of the plurality of sample vials.

27. The vial retainer system of claim 21, wherein the one or more lower surfaces comprise at least one planar ramp extending continuously from the proximal end of the vial retainer to the distal end of the vial retainer.

28. The vial retainer system of claim 21, wherein the vial retainer comprises a downwardly-facing channel having first and second downwardly-extending portions forming a first lower surface and a second lower surface.

\* \* \* \* \*